US010344010B2

(12) United States Patent
Huang et al.

(10) Patent No.: US 10,344,010 B2
(45) Date of Patent: Jul. 9, 2019

(54) METHOD FOR PURIFYING CRUDE OF 2,5-FURANDICARBOXYLIC ACID BY CRYSTALLIZATION

(71) Applicant: INDUSTRIAL TECHNOLOGY RESEARCH INSTITUTE, Hsinchu (TW)

(72) Inventors: Ying-Ting Huang, Hsinchu (TW); Jinn-Jong Wong, Hsinchu (TW); Jau-Hong Chen, Chiayi (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/830,509

(22) Filed: Dec. 4, 2017

(65) Prior Publication Data
US 2019/0127342 A1 May 2, 2019

(30) Foreign Application Priority Data
Oct. 30, 2017 (TW) .............................. 106137359 A

(51) Int. Cl.
*C07D 307/68* (2006.01)
*C08G 63/672* (2006.01)

(52) U.S. Cl.
CPC ......... *C07D 307/68* (2013.01); *C08G 63/672* (2013.01)

(58) Field of Classification Search
CPC .................................................. C07D 307/68
USPC ....................................................... 549/485
See application file for complete search history.

(56) References Cited

U.S. PATENT DOCUMENTS

| 2,811,548 | A | 10/1957 | Harn et al. |
| 2,838,565 | A | 6/1958 | Heath et al. |
| 5,961,935 | A | 10/1999 | Lee et al. |
| 8,686,186 | B2 | 4/2014 | Ure |
| 8,754,254 | B2 | 6/2014 | Bhattacharyya |
| 8,916,719 | B2 | 12/2014 | Shaikh et al. |
| 8,969,404 | B2 | 3/2015 | Janka et al. |
| 9,156,805 | B2 | 10/2015 | Shaikh et al. |
| 9,249,118 | B2 | 2/2016 | Janka et al. |
| 2016/0130244 | A1 | 5/2016 | Janka et al. |
| 2016/0207898 | A1 | 7/2016 | Singh et al. |
| 2016/0311790 | A1 | 10/2016 | Janka et al. |
| 2017/0197930 | A1 | 7/2017 | Sokolovskii et al. |

FOREIGN PATENT DOCUMENTS

| CN | 103965146 B | 4/2016 |
| CN | 105936630 A | 9/2016 |
| CN | 106117169 A | 11/2016 |
| CN | 106497957 A | 3/2017 |
| JP | 5252969 B2 | 7/2013 |
| JP | 2017-190316 A | 10/2017 |
| TW | 200502220 A | 1/2005 |
| WO | 2016-068712 A1 * | 5/2013 |
| WO | WO 2015/030590 A1 | 3/2015 |
| WO | WO 2016/195499 A1 | 12/2016 |

OTHER PUBLICATIONS

Protic Solvent, Wikipedia, http://en.wikipedia.org./wiki/Protic_solvent. Visited Jun. 29, 2016.*
Wang et al., Eu. J. Inorg. Chem. (2014), pp. 1185-1191.*
Asha et al., Dalton Trans. (2015), vol. 44, pp. 1009-1016.*
Chernyak, J. Chem. Eng. Data (2006), 51, 416-318.*
Constance, Ency. Chemical Processing & Design (1989) vol. 31, pp. 267-281.*
Taiwanese Office Action for Appl. No. 106137359 dated Jun. 27, 2018.
Wu, Z.H., et al., "Purification Method of 2,5-Furandicarboxylic Acid," Minghsin University of Science and Technology, 2011.
European Search Report for Appl. No. 18188213.5 dated Nov. 12, 2018.
Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts", Adv. Synth. Catal, 2001, vol. 343, No. 1, pp. 102-111.

* cited by examiner

Primary Examiner — Taofiq A Solola
(74) Attorney, Agent, or Firm — Birch, Stewart, Kolasch & Birch, LLP

(57) ABSTRACT

Method for purifying a crude of 2,5-furandicarboxylic acid (cFDCA) by crystallization is provided. The method includes (a) mixing the cFDCA and a solvent to form a mixture, wherein the solvent has a dipole moment of 3.7D (Debye) to 4.1D; (b) heating the mixture; (c) after step (b), cooling the mixture to precipitate a solid; and (d1) after step (c), filtering the mixture to collect a wet filter cake of the solid, and drying the wet filter cake to obtain purified FDCA. The purified FDCA has a higher FDCA purity than that of the cFDCA.

15 Claims, No Drawings

METHOD FOR PURIFYING CRUDE OF 2,5-FURANDICARBOXYLIC ACID BY CRYSTALLIZATION

CROSS REFERENCE TO RELATED APPLICATIONS

The present application is based on, and claims priority from, Taiwan Application Serial Number 106137359, filed on Oct. 30, 2017, the disclosure of which is hereby incorporated by reference herein in its entirety.

TECHNICAL FIELD

The technical field relates to a method for purifying crude of 2,5-furandicarboxylic acid (cFDCA) by crystallization, and in particular it relates to solvent utilized in the method.

BACKGROUND

Recently, biomass material has attracted a lot of attention, and 2,5-furandicarboxylic acid (FDCA) has the potential to replace terephthalic acid (TPA). The FDCA can be copolymerized with ethylene glycol (EG) to form a polyester such as polyethylene furanoate (PEF). However, the impurity content in the FDCA (e.g. 2-formyl-5-furancarboxylic acid, FFCA) may negatively influence the molecular weight and color of the polyester. The FDCA has a chemical structure of

and the FFCA has a chemical structure of

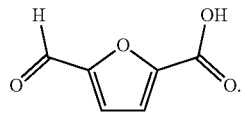

Most conventional purification methods for FDCA utilize hydrogenation or oxidation, which usually require high-temperature and high-pressure processes. Other purification methods used for the FDCA, such as the FDCA salt method, may produce a lot of waste water and cause an environmental burden. Accordingly, an easy and mild purification method for the FDCA is called-for.

SUMMARY

One embodiment of the disclosure provides a solvent for purifying a crude of 2,5-furandicarboxylic acid (cFDCA) by crystallization, comprising: a solvent having a dipole moment of 3.7D (Debye) to 4.1D.

One embodiment of the disclosure provides a method for purifying a crude of 2,5-furandicarboxylic acid (cFDCA) by crystallization, comprising: (a) mixing the cFDCA and a solvent to form a mixture, wherein the solvent has a dipole moment of 3.7D (Debye) to 4.1D; (b) heating the mixture; (c) after step (b), cooling the mixture to precipitate a solid; and (d1) after step (c), filtering the mixture to collect a wet filter cake of the solid, and drying the wet filter cake to obtain purified 2,5-furandicarboxylic acid (FDCA), wherein the purified FDCA has a higher FDCA purity than that of the cFDCA.

One embodiment of the disclosure provides a method for purifying a crude of 2,5-furandicarboxylic acid (cFDCA) by crystallization, comprising: (a) mixing the cFDCA and a solvent to form a mixture, wherein the mixture contains a solid, and the solvent has a dipole moment of 3.7D (Debye) to 4.1D; and (d2) filtering the mixture to collect a wet filter cake of the solid, and drying the wet filter cake to obtain purified 2,5-furandicarboxylic acid (FDCA), wherein the purified FDCA has a higher FDCA purity than that of the cFDCA.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details.

One embodiment of the disclosure provides a solvent for purifying a crude of 2,5-furandicarboxylic acid (cFDCA) by crystallization, which has a dipole moment of 3.7D (Debye) to 4.1D. In one embodiment, the solvent can be dimethyl sulfoxide (DMSO), dimethyl acetamide (DMAC), acetonitrile, dimethylformamide (DMF), 2-nitropropane, N-methyl-2-pyrrolidone (NMP), or a combination thereof.

In one embodiment, the cFDCA includes 80 wt % to 99 wt % of FDCA and 0.01 wt % to 10 wt % of FFCA. In one embodiment, the cFDCA includes 90 wt % to 99 wt % of FDCA and 0.01 wt % to 10 wt % of FFCA. In one embodiment, the cFDCA includes 95 wt % to 99 wt % of FDCA and 0.01 wt % to 5 wt % of FFCA. If the FDCA purity is too low, or the FFCA content is too high, the resulting purification efficiency may be too low.

In some embodiments, the method for purifying the cFDCA by crystallization includes (a) mixing the cFDCA and the solvent to form a mixture. In one embodiment, the mixing step can be stirring, supersonic vibration, or a combination thereof. The weight ratio of the cFDCA and the solvent depends on the solvent type and the FDCA purity of the cFDCA. In following Examples, the cFDCA has an FDCA purity of 98 wt %, but one skilled in the art may select another cFDCA with a different FDCA purity and not be limited to the cFDCA with an FDCA purity of 98 wt %. When the solvent is DMSO, the cFDCA and the DMSO have a weight ratio of 1:1 to 1:10. When the solvent is DMAC, the cFDCA and the DMAC have a weight ratio of 1:1 to 1:15. When the solvent is acetonitrile, the cFDCA and the acetonitrile have a weight ratio of 1:1 to 1:15. When the solvent is DMF, the cFDCA and the DMF have a weight ratio of 1:1 to 1:15. When the solvent is 2-nitropropane, the cFDCA and the 2-nitropropane have a weight ratio of 1:5 to 1:20. When the solvent is NMP, the cFDCA and the NMP have a weight ratio of 1:1 to 1:10. Too little solvent may result in the purification efficiency being too low. If there is too much solvent, the FDCA crystal cannot be obtained directly, and the product should be concentrated to obtain the FDCA crystal.

In one embodiment, the method also includes (b) heating the mixture, such as heating to a temperature of 40° C. to 120° C. The heating temperature depends on the solvent type. When the solvent is DMSO, the mixture is heated in step (b) to a temperature of 40° C. to 120° C. When the solvent is DMAC, the mixture is heated in step (b) to a temperature of 40° C. to 120° C. When the solvent is acetonitrile, the mixture is heated in step (b) to a temperature of 40° C. to 80° C. When the solvent is DMF, the mixture is heated in step (b) to a temperature of 40° C. to 120° C. When the solvent is 2-nitropropane, the mixture is heated in step (b) to a temperature of 40° C. to 100° C. When the solvent is NMP, the mixture is heated in step (b) to a temperature of 40° C. to 120° C.

The method also includes step (c) after step (b), which cools the mixture to precipitate a solid. In one embodiment, step (c) may control the mixture being cooled at a cooling rate of between 0.1° C./minute to 10° C./minute. In one embodiment, the cooling rate can be 1° C./minute. A cooling rate that is too slow causes the crystallization period to be too long, whereas a cooling rate that is too fast causes the FDCA purity of the product to be lower. In one embodiment, the method also includes step (d1) after step (c), which filters the mixture to collect a wet filter cake of the solid, and drying the wet filter cake to obtain purified FDCA. The purified FDCA obtained by step (a) to step (d1) has a higher FDCA purity than that of the cFDCA. For example, the purified FDCA may have 99 wt % to 99.9 wt % of FDCA and 0 wt % to 0.5 wt % of FFCA.

In step (d1), filtering the mixture may separate the solid and a filtrate. In one embodiment, the method may recycle the filtrate produced in step (d1), and the filtrate may directly serve as the solvent in step (a) of the subsequent round without additionally purifying the filtrate. On the other hand, the purified FDCA obtained in step (d1) can be polymerized with alkylene glycol (e.g. ethylene glycol, propylene glycol, or another suitable alkylene glycol) to form polyester, and the polyester has a weight average molecular weight that is greater than or equal to 20000. If the cFDCA (with a lower FDCA purity) is polymerized with the alkylene glycol to form polyester, the polyester cannot have a weight average molecular weight so high.

In another embodiment of the disclosure, the method for purifying the cFDCA by crystallization includes (a) mixing the cFDCA and the solvent to form a mixture. The solvent may dissolve the cFDCA, and the solute dissolved in the solvent will be precipitated to form a solid. The dissolution-precipitation phenomenon will balance after a period, which means that the solid composition in the mixture tends to be stable. In other words, the solvent in step (a) will not completely dissolve the cFDCA, and the solid exists in the mixture. For example, step (a) may continue for 1 to 3 hours to achieve a solid with a stable composition. If the period of step (a) is too short, the composition of the solid will be non-uniform, and the FDCA purity of the solid cannot be enhanced. If the period of step (a) is too long, this will increase the process time. The solvent type, the mixing method of the cFDCA and the solvent, and the weight ratio of the cFDCA to the solvent are similar to the above, and the related description is not repeated here.

In one embodiment, the method also includes step (d2) of filtering the mixture to collect a wet filter cake of the solid, and drying the wet filter cake to obtain purified FDCA. The purified FDCA obtained by step (a) to step (d2) has a higher FDCA purity than that of the cFDCA. For example, the purified FDCA may have 99 wt % to 99.9 wt % of FDCA and 0 wt % to 0.5 wt % of FFCA.

In step (d2), filtering the mixture may separate the solid and a filtrate. In one embodiment, the method may recycle the filtrate produced in step (d2), and the filtrate may directly serve as the solvent in step (a) of a subsequent round without additionally purifying the filtrate. On the other hand, the purified FDCA obtained in step (d2) can be polymerized with alkylene glycol (e.g. ethylene glycol, propylene glycol, or another suitable alkylene glycol) to form polyester, and the polyester has a weight average molecular weight that is greater than or equal to 20000. If the cFDCA (with a lower FDCA purity) is polymerized with the alkylene glycol to form polyester, the polyester cannot have a weight average molecular weight so high.

Accordingly, embodiments adopt a suitable solvent to re-crystallize the cFDCA for enhancing the FDCA purity of the purified FDCA product. Compared to conventional methods, the embodiments do not need high-temperature and high-pressure equipment. In addition, the embodiments do not produce a large amount of waste liquid. Accordingly, the cost of purifying the FDCA can be greatly reduced.

Below, exemplary embodiments will be described in detail so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1.1

75 g of DMSO and 50 g of a cFDCA (FDCA purity of 96.2 wt %, and FFCA content of 2.12 wt %) were mixed to form a mixture, which was heated to 100° C. The mixture was continuously stirred at 100° C. for 30 minutes, and then cooled to room temperature at a cooling rate of 1° C./minute. The mixture was then filtered to obtain a filter cake. The filter cake was washed with DMSO, and then dried in an oven to obtain a solid product. The FDCA purity of the solid product was analyzed by high-performance liquid chromatography (HPLC), and the results are tabulated in Table 1.

Example 1.2

100 g of DMAC and 20 g of the cFDCA (FDCA purity of 96.2 wt %, and FFCA content of 2.12 wt %) were mixed to form a mixture, which was heated to 60° C. The mixture was continuously stirred at 60° C. for 30 minutes, and then cooled to room temperature at a cooling rate of 1° C./minute. The mixture was then filtered to obtain a filter cake. The filter cake was washed with DMAC, and then dried in an oven to obtain a solid product. The FDCA purity of the solid product was analyzed by HPLC, and the results of this analysis are tabulated in Table 1.

Comparative Example 1.1

60 g of water and 2 g of the cFDCA (FDCA purity of 96.2 wt %, and FFCA content of 2.12 wt %) were mixed to form a mixture, which was heated to 60° C. The mixture was continuously stirred at 60° C. for 30 minutes, and then cooled to room temperature at a cooling rate of 1° C./minute. The mixture was then filtered to obtain a filter cake. The filter cake was washed with water, and then dried in an oven to obtain a solid product. The FDCA purity of the solid product was analyzed by HPLC, and the results of this analysis are tabulated in Table 1.

Comparative Example 1.2

100 g of methanol and 5 g of the cFDCA (FDCA purity of 96.2 wt %, and FFCA content of 2.12 wt %) were mixed to form a mixture, which was heated to 60° C. The mixture was continuously stirred at 60° C. for 30 minutes, and then cooled to room temperature at a cooling rate of 1° C./minute. The mixture was then filtered to obtain a filter cake. The filter cake was washed with methanol, and then dried in an oven to obtain a solid product. The FDCA purity of the solid product was analyzed by HPLC, and the results of this analysis are tabulated in Table 1.

TABLE 1

| Example | Solvent | Dipole moment (D) | FDCA purity of the mixture before purification (wt %) | FFCA content of the mixture before purification (wt %) | FDCA purity of the purified product (wt %) | FFCA content of the purified product (wt %) |
|---|---|---|---|---|---|---|
| Example 1.1 | DMSO | 3.96 | 96.20 | 2.12 | 97.25 | 1.17 |
| Example 1.2 | DMAC | 3.81 | | | 99.51 | 0.4 |
| Comparative Example 1.1 | Water | 1.85 | | | 96.99 | 2.0 |
| Comparative Example 1.2 | Methanol | 1.7 | | | 96.37 | 2.1 |

As shown in Table 1, the purification utilizing the solvent of DMSO or DMAC could efficiently reduce the FFCA content and enhance the FDCA purity of the product. If the purification utilized the solvent with a lower dipole moment (e.g. water or methanol), the FFCA content of the product could not be efficiently reduced, and the enhancement of the FDCA purity of the product would be limited.

Example 2.1

100 g of DMAC and 20 g of a cFDCA (FDCA purity of 98.01 wt %, and FFCA content of 0.88 wt %) were mixed to form a mixture, which was heated to 60° C. The mixture was continuously stirred at 60° C. for 30 minutes, and then cooled to room temperature at a cooling rate of 1° C./minute. The mixture was then filtered to obtain a filter cake. The filter cake was washed with DMAC, and then dried in an oven to obtain a solid product. The FDCA purity of the solid product was analyzed by HPLC, and the results of this analysis are tabulated in Table 2.

Example 2.2

20 g of DMF and 8.5 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with DMF, and then dried in an oven to obtain a solid product. The FDCA purity of the solid product was analyzed by HPLC, and the results of this analysis are tabulated in Table 2.

Example 2.3

10 g of acetonitrile and 2 g of the cFDCA (FDCA purity of 98.01 wt %, and FFCA content of 0.88 wt %) were mixed to form a mixture, which was heated to 40° C. The mixture was continuously stirred at 40° C. for 30 minutes, and then cooled to room temperature at a cooling rate of 1° C./minute. The mixture was then filtered to obtain a filter cake. The filter cake was washed with acetonitrile, and then dried in an oven to obtain a solid product. The FDCA purity of the solid product was analyzed by HPLC, and the results of this analysis are tabulated in Table 2.

Example 2.4

20 g of 2-nitropropane and 1.2 g of the cFDCA (FDCA purity of 98.01 wt %, and FFCA content of 0.88 wt %) were mixed to form a mixture, which was heated to 40° C. The mixture was continuously stirred at 40° C. for 30 minutes, and then cooled to room temperature at a cooling rate of 1° C./minute. The mixture was then filtered to obtain a filter cake. The filter cake was washed with 2-nitropropane, and then dried in an oven to obtain a solid product. The FDCA purity of the solid product was analyzed by HPLC, and the results of this analysis are tabulated in Table 2.

Example 2.5

20 g of NMP and 10 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with NMP, and then dried in an oven to obtain a solid product. The FDCA purity of the solid product was analyzed by HPLC, and the results of this analysis are tabulated in Table 2.

TABLE 2

| Example | Solvent | Dipole moment (D) | FDCA purity of the mixture before purification (wt %) | FFCA content of the mixture before purification (wt %) | FDCA purity of the purified product (wt %) | FFCA content of the purified product (wt %) |
|---|---|---|---|---|---|---|
| Example 2.1 | DMAC | 3.81 | 98.01 | 0.88 | 99.8 | 0.07 |
| Example 2.2 | DMF | 3.82 | | | 99.87 | 0 |
| Example 2.3 | Acetonitrile | 3.92 | | | 99.35 | 0.02 |
| Example 2.4 | 2-Nitropropane | 3.73 | | | 99.32 | 0.23 |
| Example 2.5 | NMP | 4.10 | | | 99.29 | 0.14 |

As shown in Table 2, the cFDCA with the FDCA purity of 98 wt % could be further purified by re-crystallization with suitable solvent. When the purification utilized DMF, the product could be free of the FFCA.

Example 3.1

10 g of NMP, 90 g of DMAC, and 10 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with a co-solvent of NMP and DMAC (w/w=1/9), and then dried in an oven to obtain a solid product. The FDCA purity of the solid product was analyzed by HPLC, and the results of this analysis are tabulated in Table 3.

Example 3.2

50 g of NMP, 50 g of DMAC, and 10 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with a co-solvent of NMP and DMAC (w/w=1/1), and then dried in an oven to obtain a solid product. The FDCA purity of the solid product was analyzed by HPLC, and the results of this analysis are tabulated in Table 3.

TABLE 3

| Example | Solvent | FDCA purity of the mixture before purification (wt %) | FFCA content of the mixture before purification (wt %) | FDCA purity of the purified product (wt %) | FFCA content of the purified product (wt %) |
|---|---|---|---|---|---|
| Example 3.1 | NMP/DMAC (w/w = 1/9) | 98.01 | 0.88 | 99.56 | 0.08 |
| Example 3.2 | NMP/DMAC (w/w = 1/1) | | | 99.42 | 0.09 |

As shown in Table 3, the co-solvent of NMP and DMAC was also suitable for re-crystallization, which could further purify the cFDCA with the FDCA purity of 98 wt %.

Example 4.1

90 g of DMAC, 10 g of DMSO, and 15 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with a co-solvent of DMAC and DMSO (w/w=9/1), and then dried in an oven to obtain a solid product. The FDCA purity of the solid product was analyzed by HPLC, and the results of this analysis are tabulated in Table 4.

Example 4.2

50 g of DMAC, 50 g of DMSO, and 15 g of the cFDCA (FDCA purity of 98.01 wt %, and FFCA content of 0.88 wt %) were mixed to form a mixture, which was heated to 80° C. The mixture was continuously stirred at 80° C. for 30 minutes, and then cooled to room temperature at a cooling rate of 1° C./minute. The mixture was then filtered to obtain a filter cake. The filter cake was washed with a co-solvent of DMAC and DMSO (w/w=1/1), and then dried in an oven to obtain a solid product. The FDCA purity of the solid product was analyzed by HPLC, and the results of this analysis are tabulated in Table 4.

TABLE 4

| Example | Solvent | FDCA purity of the mixture before purification (wt %) | FFCA content of the mixture before purification (wt %) | FDCA purity of the purified product (wt %) | FFCA content of the purified product (wt %) |
|---|---|---|---|---|---|
| Example 4.1 | DMAC/DMSO (w/w = 9/1) | 98.01 | 0.88 | 99.7 | 0.06 |
| Example 4.2 | DMAC/DMSO (w/w = 1/1) | | | 99.45 | 0.08 |

As shown in Table 4, the co-solvent of DMAC and DMSO was also suitable for re-crystallization, which could further purify the cFDCA with the FDCA purity of 98 wt %.

Example 5

In Example 2.1, the step of filtering the mixture to obtain the filter cake also produced a filtrate. 100 g of the filtrate (mainly DMAC with 6 wt % of FDCA and a little FFCA) and 20 g of the cFDCA (FDCA purity of 98.01 wt %, and FFCA content of 0.88 wt %) were mixed to form a mixture, which was heated to 60° C. The mixture was continuously stirred at 60° C. for 30 minutes, and then cooled to room temperature at a cooling rate of 1° C./minute. The mixture was then filtered to obtain a filter cake. The filter cake was washed with the filtrate, and then dried in an oven to obtain a solid product. The FDCA purity of the solid product was analyzed by HPLC, and the results of this analysis are tabulated in Table 5.

TABLE 5

| Example | Solvent | FDCA purity of the mixture before purification (wt %) | FFCA content of the mixture before purification (wt %) | FDCA purity of the purified product (wt %) | FFCA content of the purified product (wt %) |
|---|---|---|---|---|---|
| Example 2.1 | DMAC | 98.01 | 0.88 | 99.8 | 0.07 |
| Example 5 | The filtrate from Example 2.1 | | | 99.62 | 0.11 |

As shown in Table 5, the filtrate received from Example 2.1 after filtering the mixture could be used directly (without purification) to purify the cFDCA with the FDCA purity of 98 wt %.

Example 6.1

100 g of DMAC and 10 g of the cFDCA (FDCA purity of 98.01 wt %, and FFCA content of 0.88 wt %) were mixed to form a mixture, which was continuously stirred at room temperature for 60 minutes. The mixture was then filtered to obtain a filter cake. The filter cake was washed with DMAC, and then dried in an oven to obtain a solid product. The FDCA purity of the solid product was analyzed by HPLC, and the results of this analysis are tabulated in Table 6.

Example 6.2

50 g of acetonitrile and 50 g of the cFDCA (FDCA purity of 98.01 wt %, and FFCA content of 0.88 wt %) were mixed to form a mixture, which was continuously stirred at room temperature for 60 minutes. The mixture was then filtered to obtain a filter cake. The filter cake was washed with acetonitrile, and then dried in an oven to obtain a solid product. The FDCA purity of the solid product was analyzed by HPLC, and the results of this analysis are tabulated in Table 6.

TABLE 6

| Example | Solvent | FDCA purity of the mixture before purification (wt %) | FFCA content of the mixture before purification (wt %) | FDCA purity of the purified product (wt %) | FFCA content of the purified product (wt %) |
|---|---|---|---|---|---|
| Example 6.1 | DMAC | 98.01 | 0.88 | 99.5 | 0.06 |
| Example 6.2 | Acetonitrile | | | 99.2 | 0.3 |

As shown in Table 6, the suitable solvent could be mixed with the cFDCA at room temperature to enhance the FDCA purity of the product.

Example 7

In Example 6.1, the step of filtering the mixture to obtain the filter cake also produced a filtrate. 100 g of the filtrate (mainly DMAC with 5 wt % to 7 wt % of FDCA and a little FFCA) and 5 g of the cFDCA (FDCA purity of 98.01 wt %, and FFCA content of 0.88 wt %) were mixed to form a mixture. The mixture was stirred continuously at room temperature for 60 minutes, and then filtered to obtain a filter cake. The filter cake was washed with the filtrate, and then dried in an oven to obtain a solid product. The FDCA purity of the solid product was analyzed by HPLC, and the results of this analysis are tabulated in Table 7.

TABLE 7

| Example | Solvent | FDCA purity of the mixture before purification (wt %) | FFCA content of the mixture before purification (wt %) | FDCA purity of the purified product (wt %) | FFCA content of the purified product (wt %) |
|---|---|---|---|---|---|
| Example 6.1 | DMAC | 98.01 | 0.88 | 99.5 | 0.06 |
| Example 7 | The filtrate from Example 6.1 | | | 99.5 | 0.07 |

As shown in Table 7, the filtrate received from Example 6.1 after filtering the mixture could be used directly (without purification) to purify the cFDCA with the FDCA purity of 98 wt %.

It will be apparent to those skilled in the art that various modifications and variations can be made to the disclosed methods and materials. It is intended that the specification and examples be considered as exemplary only, with the true scope of the disclosure being indicated by the following claims and their equivalents.

What is claimed is:

1. A method comprising purifying a crude of 2,5-furandicarboxylic acid (cFDCA) by crystallization, said cFDCA comprising 80 wt % to 99 wt % of FDCA and 0.01 wt % to 10 wt % of 2-formyl-5-furancarboxylic acid (FFCA), said method comprising:
   (a) mixing the cFDCA and a solvent to form a mixture, wherein the solvent is dimethylacetamide, acetonitrile, dimethylformamide, 2-nitropropane, N-methyl-2-pyrrolidone, or a combination thereof, wherein, when the solvent is dimethylacetamide, the cFDCA and the dimethylacetamide have a weight ratio of 1:1 to 1:15, when the solvent is acetonitrile, the cFDCA and the acetonitrile have a weight ratio of 1:1 to 1:15, when the solvent is dimethylformamide, the cFDCA and the dimethylformamide have a weight ratio of 1:1 to 1:15, when the solvent is 2-nitropropane, the cFDCA and the 2-nitropropane have a weight ratio of 1:5 to 1:20, and when the solvent is N-methyl-2-pyrrolidone, the cFDCA and the N-methyl-2-pyrrolidone have a weight ratio of 1:1 to 1:10;
   (b) heating the mixture;
   (c) after step (b), cooling the mixture to precipitate a solid; and
   (d1) after step (c), filtering the mixture to collect a wet filter cake of the solid, and drying the wet filter cake to obtain purified 2,5-furandicarboxylic acid (FDCA), wherein the purified FDCA has a higher FDCA purity than that of the cFDCA.

2. The method as claimed in claim 1, wherein step (a) of mixing the cFDCA and a solvent to form a mixture comprises stirring, supersonic vibration, or a combination thereof.

3. The method as claimed in claim 1, wherein the cFDCA comprises 90 wt % to 99 wt % of FDCA and 0.01 wt % to 10 wt % of FFCA.

4. The method as claimed in claim 1, wherein the cFDCA comprises 95 wt % to 99 wt % of FDCA and 0.01 wt % to 5 wt % of FFCA.

5. The method as claimed in claim 1, wherein step (b) comprises heating the mixture to a temperature of 40° C. to 120° C.

6. The method as claimed in claim 1, further comprising recycling a filtrate produced by step (d1), and the filtrate serves as the solvent in step (a) of a subsequent round.

7. The method as claimed in claim 1, wherein the purified FDCA comprises 99 wt % to 99.9 wt % of FDCA and 0 wt % to 0.5 wt % of FFCA.

8. The method as claimed in claim 1, wherein the purified FDCA is applied to be copolymerized with alkylene glycol to form polyester, and the polyester has a weight average molecular weight that is greater than or equal to 20000.

9. A method comprising purifying a crude of 2,5-furandicarboxylic acid (cFDCA) by crystallization, said cFDCA comprising 80 wt % to 99 wt % of FDCA and 0.01 wt % to 10 wt % of 2-formyl-5-furancarboxylic acid (FFCA), said method comprising:
   (a) mixing the cFDCA and a solvent to form a mixture, wherein the solvent is dimethylacetamide, acetonitrile, dimethylformamide, 2-nitropropane, N-methyl-2-pyrrolidone, or a combination thereof, wherein, when the solvent is dimethylacetamide, the cFDCA and the dimethylacetamide have a weight ratio of 1:1 to 1:15, when the solvent is acetonitrile, the cFDCA and the acetonitrile have a weight ratio of 1:1 to 1:15, when the solvent is dimethylformamide, the cFDCA and the dimethylformamide have a weight ratio of 1:1 to 1:15, when the solvent is 2-nitropropane, the cFDCA and the 2-nitropropane have a weight ratio of 1:5 to 1:20, and when the solvent is N-methyl-2-pyrrolidone, the cFDCA and the N-methyl-2-pyrrolidone have a weight ratio of 1:1 to 1:10; and
   (d2) filtering the mixture to collect a wet filter cake of the solid, and drying the wet filter cake to obtain purified 2,5-furandicarboxylic acid (FDCA), wherein the purified FDCA has a higher FDCA purity than that of the cFDCA.

10. The method as claimed in claim 9, wherein step (a) of mixing the cFDCA and a solvent to form a mixture comprises stirring, supersonic vibration, or a combination thereof.

11. The method as claimed in claim 9, wherein the cFDCA comprises 90 wt % to 99 wt % of FDCA and 0.01 wt % to 10 wt % of FFCA.

12. The method as claimed in claim 9, wherein the cFDCA comprises 95 wt % to 99 wt % of FDCA and 0.01 wt % to 5 wt % of FFCA.

13. The method as claimed in claim 9, further recycling a filtrate produced by step (d2), and the filtrate serves as the solvent in step (a) of a subsequent round.

14. The method as claimed in claim 9, wherein the purified FDCA comprises 99 wt % to 99.9 wt % of FDCA and 0 wt % to 0.5 wt % of FFCA.

15. The method as claimed in claim 9, wherein the purified FDCA is applied to be copolymerized with alkylene glycol to form polyester, and the polyester has a weight average molecular weight that is greater than or equal to 20000.

* * * * *